US006033889A

United States Patent [19]

Han et al.

[11] Patent Number: 6,033,889

[45] Date of Patent: Mar. 7, 2000

[54] **GENE SEQUENCE OF *AQUIFEX PYROPHILUS* SUPEROXIDE DISMUTASE AND PROTEIN EXPRESSED IN *ESCHERICHIA COLI***

[75] Inventors: Ye Sun Han; Yeon Gyu Yu, both of Seoul, Rep. of Korea; Sung Hou Kim, Berkeley, Calif.; Jae Hwan Lim, Kwachun, Rep. of Korea; Jae Ryeon Ryu; In Geol Choi, both of Seoul, Rep. of Korea

[73] Assignee: Korea Institute of Science and Technology, Seoul, Rep. of Korea

[21] Appl. No.: 09/008,303

[22] Filed: Jan. 16, 1998

[30] Foreign Application Priority Data

Jan. 16, 1997 [KR] Rep. of Korea ........................ 97-1140

[51] Int. Cl.$^7$ ............................ C12N 9/02; C12N 15/00; C12N 5/00; C12P 21/06

[52] U.S. Cl. .................... 435/189; 435/69.1; 435/320.1; 435/325; 435/252.8; 536/23.1; 536/23.2; 536/24.3; 536/24.32

[58] Field of Search ................................ 435/69.1, 320.1, 435/325, 252.8, 189; 536/23.1, 23.2, 24.3, 24.32

[56] References Cited

PUBLICATIONS

Lim, J.–H. et al., FEBS Letters, vol. 406, pp. 142–146, Apr. 7, 1997.

Charles Beauchamp, et al., Analytical Biochemistry, vol. 44, pp. 276–287, 1971, "Superoxide Dismutase: Improved Assays and an Assay Applicable to Acrylamide Gels[1]".

Irwin Fridovich, Annu. Rev. Biochem., vol. 64, pp. 97–112, 1995, "Superoxide Radical and Superoxide Dismutases".

Showbu Sato, et al., Eur. J. Biochem., vol. 73, pp. 373–381, 1977, "Superoxide Dismutase From Thermus Aquaticus".

M. Takao, et al., The Journal of Biological Chemistry, vol. 266, No. 22, pp. 14151–14154, 1991, "Unique Characteristics of Superoxide Dismutase of a Strictly Anaerobic Archaebacterium Methanobacterium Thermoautotrophicum".

J.M. McCord, et al., Oxidases and Related Redox Systems, vol. 1, University Park Press, p. 51–76, 1973, "Superpoxide and Superoxide Dismutase".

H.M. Hassan, et al., Proc. Natl. Acad. Sci. USA, vol. 89, pp. 3217–3221, 1992, "Regulatory Roles of FNR. Fur, and Arc in Expression of Manganese–Containing Superoxide Dismutase in *Escherichia Coli*".

Y. Takeda, et al., Nucleic Acids Research, vol. 14, No. 11, pp. 4577–4590, 1986, "Structure and Gene Expression of the *E. Coli* MN–Superoxide Dismutase Gene".

I. Fridovich, Adv. Enzymol., vol. 58, pp. 61–97, 1986, "Superoxide Dismutases".

L. Flohe, et al., pp. 93–105, "Superoxide Dismutase Assays" Methods in Enzymology vol. 105, 1984.

*Primary Examiner*—Ponnathapu Achutamurthy
*Assistant Examiner*—Peter P. Tung
*Attorney, Agent, or Firm*—Oblon, Spivak, McClelland, Maier & Neustadt, P.C.

[57] ABSTRACT

Gene sequences of superoxide dismutase of *Aquifex pyrophilus* which is one of hyperthermophile microorganism and protein expressed therefrom are provided, wherein the protein is used as a necessary medicament in treatment of inflammation, disease of autoimmunization, chromosome lesion and the like, and particularly, *A. pyrophilus* is a hyperthermophile which can grow at the optimum temperature of 85° C., and thus the superoxide dismutase of *A. pyrophilus* has a higher thermal stability than other organisms, resulting in further broad applications in the pharmaceutical field.

9 Claims, 9 Drawing Sheets

```
1    GAGCTCCTGGGCGAACTCGTCGTTGAGTTCGGGGAGAACCTTCTTCTTTATCTCCTTTATCTTAACCTTTATATTTACCTTCCTTATCTCCTTGCCTTCCTGGTCGTACAGGGGAAGC

119  TCTTTCAGCTCTACCTCTTCTCCCGCCTTCTTTCCTTTAAGGGCTTCCTCTACTTCCTTTCTCAGCATTCCCTGGCCGAGTATCACCGAGGTTTCCTGCTTTACCTTTTCCCCTTCACCG

239  CCAACCTCTTCAACTTCGTACTCAAGGACGAGCATATCCCCCTCTTGGGCCGGCTCGTTCTCTTCCTTTGGGTTCCCAAACCGCGTTAGCCTCTCTTAGTCTTTCAAGCTCTTCCTTACA

359  TACTCCTCCTTGAACTCTATCTTGGGAACTTCTACCTCAAGGTCTGCGATGTTTTTTAGCTCAAACTCTGGAGCGACTTCAAAGCTAACGGTGTATTTTACGCTTCCCTCTTCCTCATTT

479  ACCTCAAGTTTTTCAAGGAATACGTCCGCAACGGGTCTTATATTTGCCTTCTCAAGGGCTTCCTGGAGTGTTTCGTCCGCTATTTTCTTTCCAACCTCTTCCTCCACGTAGTCCTTATAC

599  TTCGCTCTAATTATCCAGAGTGGGGCTTTTCCCCTTCTGAATCCCTGTATCTGGACGTTCTGCTGCAGGTTCTTGTAGGTTTCCTCAAGTTTTTCCTTAACCTTTTGGTCCTTTACCTCA

719  ACCGTTAGGGATTTAAAGAGTCCTTCCCTGTCCTGAACCTCTACTTTCATTACGACCTCCGTCTATTTTACTGGTGCGGGTGGCGGGAGTCGAACCCGCACGCCCTTACGGGCACCGGAT

839  CCTAAGTCCGGCGCGTCTGCCAGTTCCGCCAACACCCGCTAAATAAATTATTATATAGTTCGCAAACGTGAAAAAAAGAATCCTTTCTTTTATGACCTTAGGCATATAAAACCTTAAAAC

959  TTCCAAGTTAAAATTTTTAAATAGAAAAAAGCTAACGAAAAGGAGGTGGCAAAAATGGGTGTGCACAAACTGGAACCCAAAGACCATTTAAAACCTCAAAACCTTGAGGGTATATCTAAC
                                                           (M) G  V  H  K  L  E  P  K  D  H  L  K  P  Q  N  L  E  G  I  S  N

1079 GAACAGATAGAACCCCACTTTGAGGCACACTACAAGGGTTACGTTGCAAAGTATAACGAGATTCAGGAGAAACTCGCGGACCAGAACTTTGCGGACAGAAGCAAGGCAAACCAGAACTAC
     E  Q  I  E  P  H  F  E  A  H  Y  K  G  Y  V  A  K  Y  N  E  I  Q  E  K  L  A  D  Q  N  F  A  D  R  S  K  A  N  Q  N  Y

1199 TCCGAATACAGGGAGTTGAAGGTTGAAGAAACTTTTAACTACATGGGGGTGGTGCTCCACGAGCTTTACTTCGGCATGCTCACGCCTGGTGGAAAGGGAGAACCCTCCGAAGCCCTCAAG
     S  E  Y  R  E  L  K  V  E  E  T  F  N  Y  M  G  V  V  L  H  E  L  Y  F  G  M  L  T  P  G  G  K  G  E  P  S  E  A  L  K
```

*FIG. 3A*

```
1319 AAGAAGATTGAAGAGGATATCGGAGGACTTGATGCCTGCACGAACGAGCTAAAGGCCGCAGCTATGGCCTTCAGGGGATGGGCTATACTCGGGCTTGACATATTCAGCGGAAGGCTCGTG
     K  K  I  E  E  D  I  G  G  L  D  A  C  T  N  E  L  K  A  A  A  M  A  F  R  G  W  A  I  L  G  L  D  I  F  S  G  R  L  V

1439 GTTAACGGACTTGACGCCCACAACGTTTATAACTTAACGGGACTCATTCCCCTCATAGTTATAGACACTTATGAACACGCCTACTACGTTGACTACAAGAACAAGAGACCTCCTTACATT
     V  N  G  L  D  A  H  N  V  Y  N  L  T  G  L  I  P  L  I  V  I  D  T  Y  E  H  A  Y  Y  V  D  Y  K  N  K  R  P  P  Y  I

1559 GACGCATTCTTCAAGAACATAAACTGGGACGTCGTTAACGAAAGGTTTGAAAAGGCTATGAAAGCTTACGAGGCCCTCAAGGACTTCATCAAGTAAGCTTGCTCCCTTTTCTCCTTTCCC
     D  A  F  F  K  N  I  N  W  D  V  V  N  E  R  F  E  K  A  M  K  A  Y  E  A  L  K  D  F  I  K

1679 TTCTCCTTATCCTATCCTGCGGGTATAAAAAGCTCTCCAAAACCACTCCCGGAACCAATTTTTACACTTAAAAGAATCGGAGATTACGTTTACGTAATAGGCGAGGACATTGAGGTAAAG

1799 GGCTTTAAAAAGCATAAAAACTTCTGGTATAAGAAGGAAGAAAGGGCCTTCTGTTTTTACGTTAAGCATGTTAAAGGTAAAGAGAAAAAAGCCTGCGTTCCCGAGGCGGGTCGGATAAAG

1919 CCGAGAATTTCATACGAAGAGAAAGAAGAGAAGGTCATTATAAGGGCTGAGGAAAAGGGAATTTACAACGTTTATCCTTATGAGGGAAACCTATTGATACCTTTTCCCTTAAAAACCTTT

2039 GAAGACTCTGCAGAGcTC
```

*FIG. 3B*

M: MOLECULAR WEIGHT MARKER
1: BL21-pET3d
2: BL21-pD27
3: AQUEOUS LAYER AFTER CENTRIFUGATION
4: AQUEOUS LAYER AFTER HEATING AT 80°C FOR 60 MIN
5: PURIFIED SOD (1) ALCOHOL DEHYDROGENASE, YEAST (150,000 Da)

(2) BOVINE SERUM ALBUMIN MONOMER (66,000 Da)

(3) CABONIC ANHYDRASE, BOVINE ERYTHROCYTES (29,000 Da)

(A) STAINING WITH COOMASSIE BRILLIANT BLUE
(B) STAINING WITH NBT, 20mM POTASSIUM PHOSPHATE, pH 7.0 FOR 1 HOUR
(C) STAINING WITH NBT, 20mM POTASSIUM PHOSPHATE CONTAINING 10mM KCN, pH 7.0 FOR 1 HOUR
(D) STAINING WITH NBT, 20mM POTASSIUM PHOSPHATE CONTAINING 40mM $H_2O_2$, pH 7.0 FOR 1 HOUR (A) STAINING WITH COOMASSIE BRILLIANT BLUE
(B) STAINING WITH NBT

LANE 1: Fe-FREE A. PYROPHILUS SOD

LANE 2: Fe-REBOUND A. PYROPHILUS SOD, WITH HEATING AT 95°C, FOR 10 MIN

LANE 3: Fe-REBOUND A. PYROPHILUS SOD, WITHOUT HEATING

GENE SEQUENCE OF *AQUIFEX PYROPHILUS* SUPEROXIDE DISMUTASE AND PROTEIN EXPRESSED IN *ESCHERICHIA COLI*

BACKGROUND OF THE INVENTION

1. Field of the Invention

The present invention relates to a gene sequence of superoxide dismutase of *Aquifex pyrophilus* and protein expressed in *Escherichia coli.*

2. Description of the Prior Art

Recently, there has been a variety of attempts to isolate enzymes from the organisms which may grow in a specific environment, or to modify a known enzyme so as to obtain an enzyme which can maintain its activity in a specific environment. In particular, the presence of an organism which can grow in temperatures around 100° C. or higher has been reported, and it has been known that an enzyme isolated from such a organism can also maintain its activity at a high temperature of around 100° C. without being denatured. Therefore, there have been extensive attempts to find a hyperthermophilic enzyme which is active at a high temperature from such microorganisms. Microorganisms which may grow at an extremely high temperature are collectively referred to as "hyperthermophile" and their optimum growth temperature is normally a temperature of at least 80° C. It has also been reported that some kinds of microorganisms may grow even at an extremely higher temperature of at least 115° C. Now, it has been reported that there are about at least 50 to 60 kinds of hyperthermophile, and they are largely distributed at deep thermal vent regions. Most hyperthermophile are classified as a kind of archaeobacteria or archaea, among which are two species of *Thennotoga* and *Aquifex* which belong to a class of bacteria.

The results of 16s RNA sequence analysis indicated that *A. pyrophilus* of Eubacterium is located at the lowest part of the evolution map. They are known as an autotrophic bacterium which can oxidize or reduce sulfur atom to produce energy. [See, Huber R. et al., *Syst. Appl. Microbiol.* 15: 349–351, 1992]. *A. pyrophilus* was discovered in deep submarine. It also has been found that the organism may grow between 67° C. and 95° C. and its optimum growth temperature is 85° C.

Superoxide dismutase (hereinafter. referred to SOD) is an enzyme which can convert superoxide radicals ($O_2$—) to $H_2O_2$. The superoxide radicals are chemically and inevitably generated in vivo. The enzyme is one of the important enzymes to function in the intracellular protection mechanisms. [See, Fridovich, I. et al., *Annu. Rev. Biochem.* 64, 97–112]. SODs are divided into three species, i.e., Cu- and Zn-, Fe-, and Mn-SOD in accord with the kind of bound metal. Cu-, and Zn-SOD are found in eucaryote, Fe-SOD in eubacteria and archaeobacteria, and Mn-SOD in bacteria and mitochondria of eucaryote.

As disclosed above, the superoxide dismutase involves an important protection mechanism to prevent cellular lesions due to oxygen. Therefore, the enzyme may be useful for the preparation of necessary medicaments for treating inflammation, disease of autoimmunization, chromosomal lesion and the like. Particularly, *A. pyrophilus* is one of hyperthermophilic bacteria which can grow at the optimum temperature of 85° C., so that the superoxide dismutase of *A. pyrophilus* has a higher thermal stability than other organisms and is further broadly applicable in the field of the pharmaceutical industry.

BRIEF DESCRIPTION OF THE SEVERAL VIEWS OF THE DRAWING

FIG. 3 is a gene sequence of pD2 clone containing SOD gene (SEQ ID NO: 1 and 2).

SUMMARY OF THE INVENTION

The object of the present invention is to obtain a superior superoxide dismutase in thermal stability. This object is accomplished by finding gene sequences of the superoxide dismutase from *A. pyrophilus* and expressing proteins in *E. coli* to produce a superior enzyme in thermal stability.

DETAILED DESCRIPTION OF THE INVENTION

Figure 1:
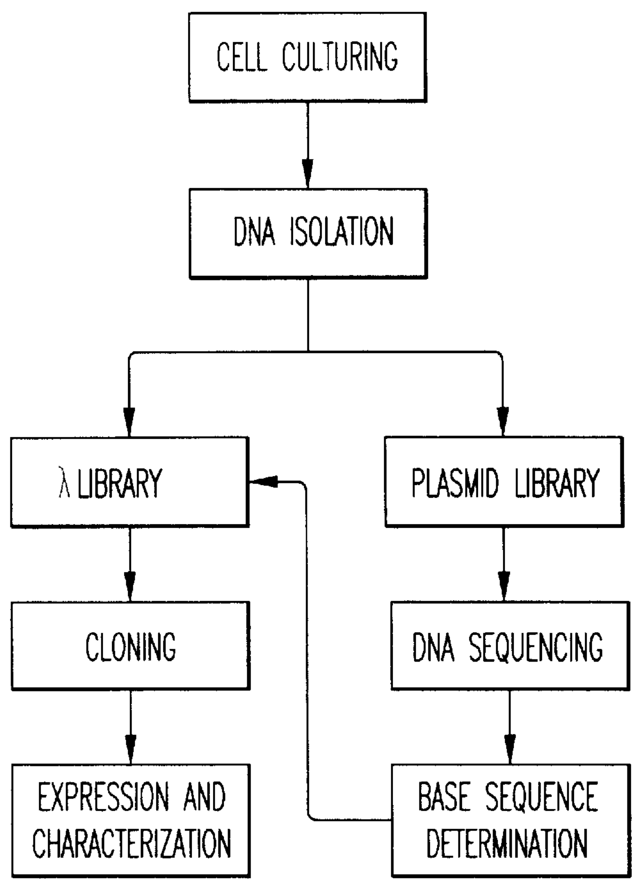
FIG. 1 is a flow chart according to the present invention.

The gene sequences of superoxide dismutase of the present invention are isolated from *A. pyrophilus* strain (DSM #6858) which has been deposited with the deposit authority, DSM (Deutsche Sammiung von Mikroorganism und Zellkulturen GmBH) in Germany. The strain culturing [See, Huber, R. et al., *Syst. Appl. Microbiol.*, 15:349–351, 1992], genomic DNA isolation from the strain and then cloning of the genomic DNA are carried out, as shown in FIG. 1. Plasmid library and genomic library are prepared by using pBluescript KS(+) and λDASHII, respectively. The gene sequences of about 178 clones of the plasmid library are read by the chain termination method, and then a similarity to other SOD species is searched in BLAST program (Basic Local Alignment Search Tool Program). Polymerase chain reaction of the most similar clone is carried out and the produced synthetic segments is used as a probe for finding the SOD gene from the genomic library in order to obtain an entire SOD gene.

Figure 2:
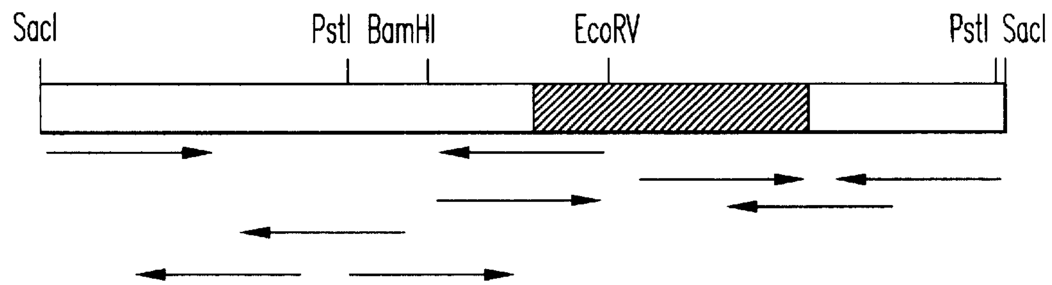
FIG. 2 is a strategy for mapping the restriction enzyme and sequencing the gene sequences of *A. pyrophilus* SOD.

A genomic DNA library was plated on *E. coli* MRA-P2. Plaque hybridization screening was done using ECL direct system (Amersham Co., Ohio, U.S.A.). Prehybridization and hybridization were done at 42° C. for 1 and 4 h, respectively, in hybridization solution. Positive plaques were pooled in SM buffer (50 mM Tris-HCl, pH 7.5, 10 mM NaCl, 8 mM $MgSO_4$, 0.01% gelatin), replated at low density, and a single plaque was isolated. Phage DNA was isolated using Qiagen Lambda Kit. Phage DNA digested with HindIII, EcoRI, and SacI were identified by Southern hybridization with the PCR-amplified fragment as a probe. The phage DNA ((φ12) digested with SacI was ligated with pBluscript KS(+) and transformation of *E. coli* DH5α was carried out according to the procedure by Sambrook. The positive clones were tested by PCR to yield a final clone, pD2. The pD2 clone which had the SOD gene was digested with SacI, EcoRV, PstI and BamHI as shown in FIG. 2. These fragments were subcloned into pBluescript KS(+) for DNA sequencing (See, FIG. 3).

The identified gene sequence according to the present invention consist of a total of 639 bases, wherein initiation codon is ATG codon at the position of 1,013 and termination codon is TAA codon at the position of 1,652. GAAAAG-GAGG (SEQ ID NO: 3) is present at the position of 18 bases upstream the initiation codon, which is similar to the Shine Dalgarno base sequence for *E. coli* and which is presumed to be a ribosome-binding position. TATAAA (SEQ ID NO: 4) at the position of 70 base upstream the initiation codon is considered to be a promoter position.

To express proteins from the identified gene, pD2 clones containing the SOD gene are subjected to the polymerase chain reaction using two synthetic primers. Synthetic fragments obtained from the reaction are treated with restriction enzyme NcoI and BamHI, ligated to pET3d vector (Novagen, Inc.) which has been pretreated with the same enzymes, and then transformed to host, *E. coli* BL21. The sequences of synthetic primers used are as follows.

sodF (SEQ ID NO: 5):

5'-GCCTCACGTTCACCATGGGTGTGCACAAACTGGA ACCCAAAG-3' sodR (SEQ ID NO: 6):

5'-GCTAGGCATGTCGGACTTTTACTTGATGAAGTCCT TGAGGGC-3'

Figure 4:
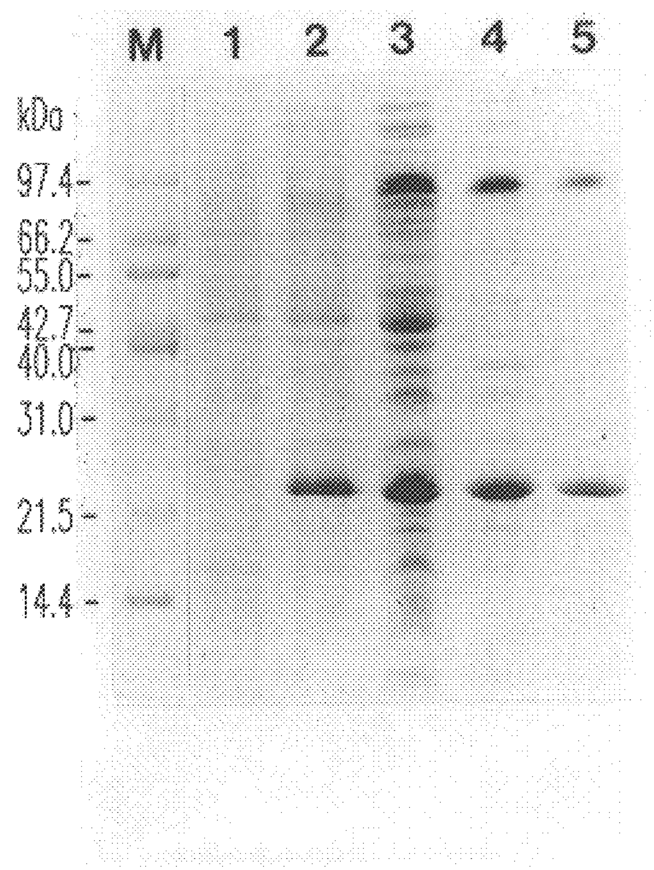
FIG. 4 is a photograph showing Tricine-SDS polyacrylamide gel (16.5%) electrophoresis of SOD protein in every purification step.

Several recombinant clones are inoculated to the ampicillin-added LB medium and a test of SOD expression is conducted by employing SDS-PAGE. The strongest expressed recombinant clone (pD27) is selected. IPTG is added to *E. coli* BL21 culture (which has been deposited with the Korea Research Institute of Bioscience and Biotechnology, Korean Collection for Type Cultures at #52, Oun-dong, Yusong-ku, Taejon 305–333, Republic of Korea and designated as KCTC 0288BP) in which plasmid pD27 containing SOD gene resides, inducing proteins therefrom. Then, the proteins are isolated and purified by using anionic exchange chromatograph (Q-sepharose, FPLC, LKB Pharmacia) and Gel-filtration column. The purified proteins are analysed for their protein size on a 16.5% Tricine SDS-PAGE to identify as 24 kDa and 96 kDa (See, FIG. 4). The protein of 24 kDa has the same molecular weight as calculated from the predicted amino acid sequence from its base sequence. The 96 kDa protein shows that SOD of *A. phraphilus* is present in a form of homotertramer, which is consistent with the crystalline structure of SOD.

Figure 5:
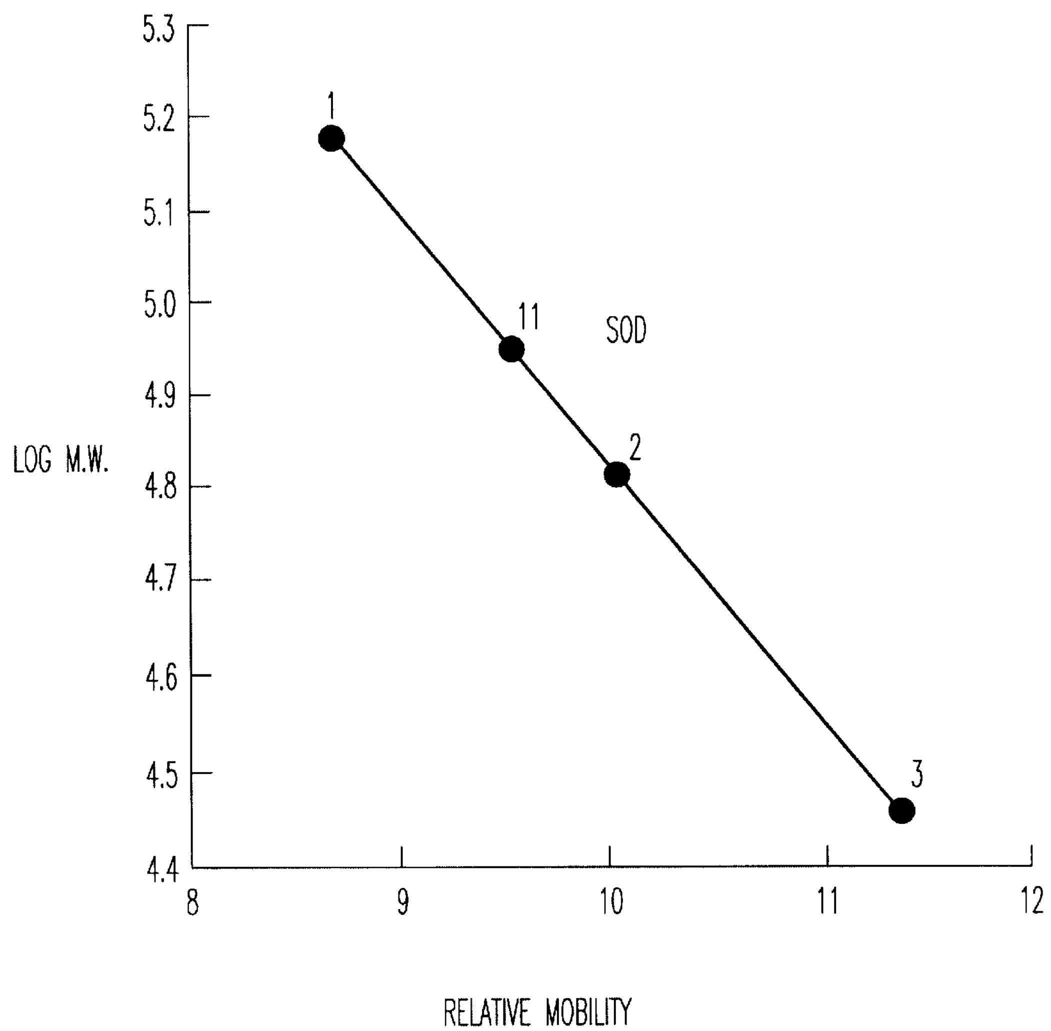
FIG. 5 is a graph showing the results of Sephacryl S-200 gel-filtration chromatography for determining the molecular weight of *A. pyrophilus.*

Sephacryl S-200 gel filtration chromatography is used to determinate the molecular weight of SOD. The molecular weight of SOD is 89 kDa (See, FIG. 5). Atomic Absorption Spectrophotometer (Barian SectrAA800) is used to analyse what kind of metal is contained in a purified protein. It is found that the SOD contains 0.75 gram atom of iron per monomer.

The nitro blue tetrazolium (NBT) staining method is used to test the activity of enzymes [See, Beauchamp, C. and Fridovich, I., Anal. Biochem, 44:276–287, 1971]. Superoxide radicals can reduce colorless nitro blue terzolium to blue formazan, whereas active sites of the SOD protein immobilized on the gel appear as transparent bands. In this method, it is found that KCN renders Cu-, Zn-SOD inactive and $H_2O_2$ inhibits the activity of Fe-SOD. It was identified that the SOD protein of *A. pyrophilus* contains Fe, because the protein is inactivated by $H_2O_2$ (See, FIG. 6). From the comparison of the activity of Fe-free SOD and Fe-rebound SOD, it is found that Fe-free SOD is present as inactive monomers and Fe-rebound SOD is present as a mixture of active tetramers and inactive monomers (See, FIG. 7).

To determinate the activity of SOD protein, cytochrome c reduction determination method is used (See, Fridovich, I., *Adv. Enzymol.* 58: 61–87, 1986). SOD activity unit is defined as the amount of enzyme which inhibits the rate of cytochrome c reduction by 50%.

Figure 8:
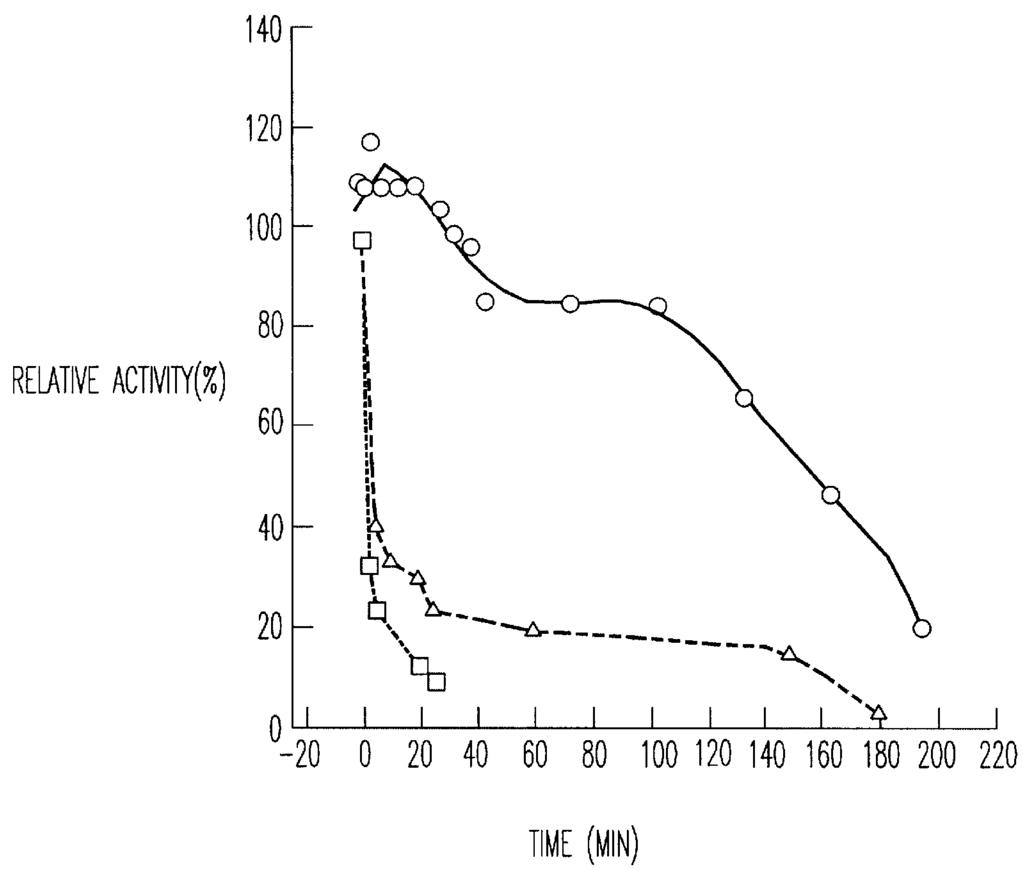
FIG. 8 is a graph showing comparisons of specific activities of *A. pyrophilus* SOD, *E. coli* Fe-SOD and *Bacillus stearothennophilus* Mn-SOD after heating the SODs.
Figure 9:
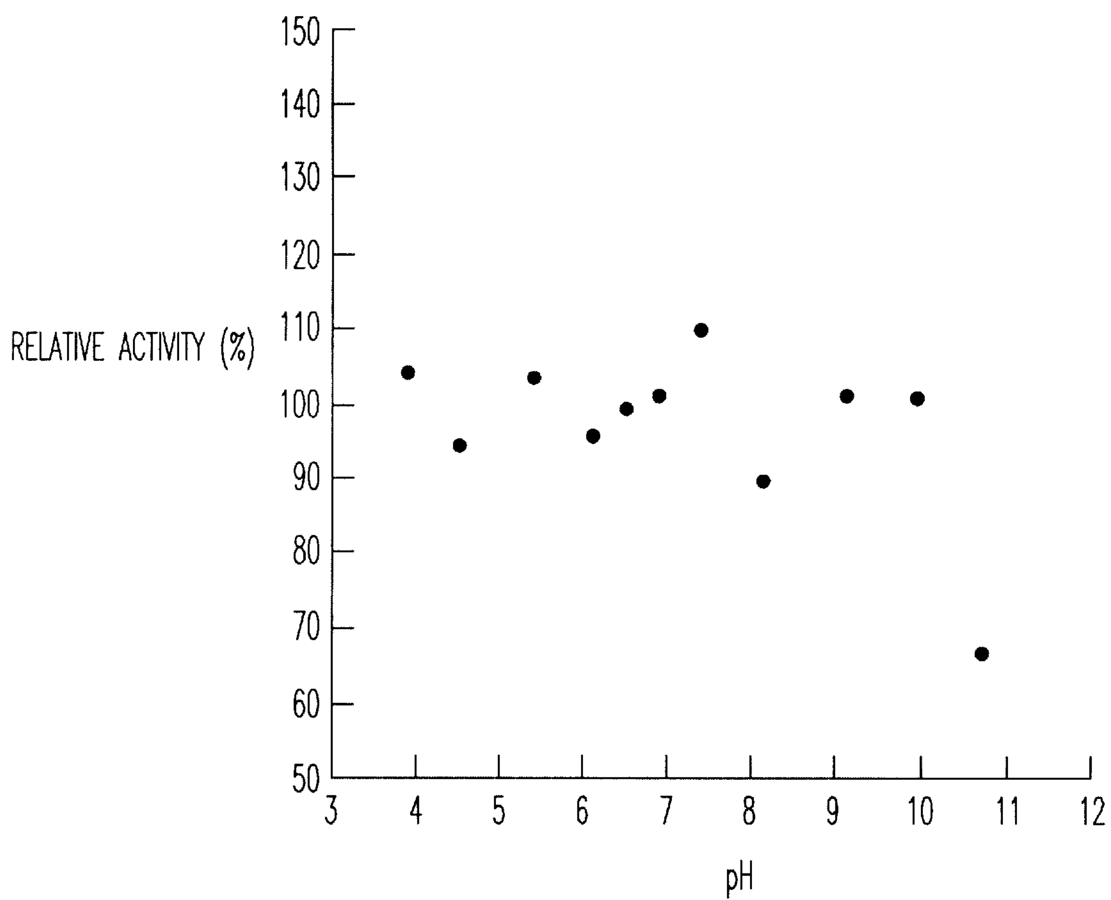
FIG. 9 is a graph showing the determination of activity of SOD between pH 4.0 and pH 10.7, on which the effect of pH on activity is indicated.

While the specific activity of SOD of *A. pyrophilus* is 1,400 unit/mg, those of Fe-SOD of *E. coli* and Mn-SOD of *Bacillus stearothennophilus* are 1,623 unit/mg and 1,387 unit/mg, respectively. Their activities at a normal temperature are similar to one another. By using cytochrome c reduction determination method, thermostability of the enzymes are determinated. After boiling for 2 hours, SOD of *A. pyrophilus* retains about 80% of activity (See, FIG. 8). To the contrary, after boiling at 95° C. for 2 hours Fe-SOD of *E. coli* and Mn-SOD of *Bacillus stearothermophilus* lose almost all of their activities. Thus, the results show that SOD of *A. pyrophilus* has strong thermostability, as predicted.

Examination of the activity of SOD at normal temperature in cytochrome c reduction determination method for testing the stability of the enzyme at various pH phases identified that the enzyme shows its activity and loses no activity, within a range of pH 4.0 to pH 10.7.

DESCRIPTION OF THE PREFERRED EMBODIMENTS

The present invention will be illustrated in greater detail by way of the following examples. The examples are presented for illustrative purposes only and should not be construed as limiting the invention.

EXAMPLE 1

Cloning of Superoxide Dismutase Gene

As shown in FIG. 1, a gene cloning flow chart was designed for obtaining a gene to produce superoxide dismutase. *A. pyrophilus* strain (DSM #6858) is available from DSM (Deutsche Sammlung von Mikroorganismen und Zellkulturen Gmbh) which is an Microorganism deposition authority in Germany. A plasmid library from the strain was prepared as follows. The strain was cultured to yield genomic DNA and then the resulting genomic DNA was treated with restriction enzyme HindIII to produce small gene fragments. The resulting DNA fragments were cloned into vector pBluescript KS (±) which has been lineared by digesting with HindIII, to screen 178 positive clones containing the *A. pyrophilus* gene. Screening was conducted in a medium containing X-gal and IPTG (isopropyl-1-thio-beta-D-galactosidase) by using alpha-complement test in a known method. Base sequences of these clones were determinated in dideoxynucleoside chain termination method. Among them, a single clone of which sequence is similar to the SOD sequence derived from other species was found and designated as aqpksH15.

For obtaining insert segments containing a portion of SOD gene in aqpksH15, polymerase chain reaction was conducted (T7, KS primer; at 95° C. for 1 min 30 sec; at 50° C. for 1 min; 72° C. for 1 min/25 times cycle). Synthetic segments thus obtained, were used as a probe for finding the SOD gene from the genomic library in order to obtain an entire SOD gene. AqpksH15 was treated with restriction enzyme HindII and EcoRV and the obtained DNA segments (400 bp) were isolated on agarose gel. The isolated DNA was used as a probe to establish a gene map of an entire SOD gene obtained after they were probed.

Genomic DNAs for *A. pyrophilus* (DSM 36858) were incompletely excised with HindIII to obtain segments in an appropriate size (at least 10 kb), and then linked to the HindIII-digested lamda-DASH II DNA (available from Stratagene, Calif., U.S.A.) to package the genomic library by using Gigapack XL packaging extract (available from Stratagene, La Jolla, Calif., U.S.A.). Thereafter, the genomic library was completed using the method described by Sambrook, et al., Molecular Cloning: A Laboratory Manual, 2nd ed., Cold Spring Harbor laboratory Press, Cold Spring Harbor, N.Y., (1989). The plaque forming unit of the prepared library was about $10^{10}$ pfu/ml.

To obtain an entire gene of SOD from the genomic library thus obtained of *A. pyrophilus*, the amplified segment obtained above was used as a probe to conduct plaque-bindinga detection method by using ECL Direct System (available from Amersham Co.). 12 clones which show a positive signal were selected, among which a clone showing the strongest positive signal was selected and designated as A12. Clone A12 contained 2.1 kb *A. pyrophilus* gene insert segments. Following extraction of DNAs from the segments, the DNAs were treated with restriction enzyme SacI to conduct an analysis of Southern blotting hybridization. At this time, 2.1 kb insert segments were isolated from the agarose gel, which show a positive signal, and then linked to the SacI-pretreated pBluscript SK(±). The resulting clones were designated as pD2. Restriction enzyme positions which are contained within the 2.1 kb segment of the clone, were used to treat the segment and vector with restriction enzyme PstI, BamHI, EcoRV, respectively and subcloned them into pBluescript SK(±) (See, FIG. 2). From each of the resulting clones, entire 2.1 kb base sequences were determinated using dideoxynucleoside chain termination method (See, FIG. 3). Comparative analysis of the base sequence with the known superoxide dismutase gene sequence of other species, identified that the resulting base sequences shows high homology to SOD of *E. coli* in 44%, to SOD of *Bacillus stearothermophilus* in 45%, and to SOD of *Thermus thenmophilus* in 45%.

EXAMPLE 2

Expression, Isolation and Purification of Superoxide Dismutase Protein

After checking the restriction enzyme and base sequences in order to obtain superoxide dismutase protein, the protein was expressed in *E. coli* of which a protein expression mechanism is well established presently. First, expression vector pET3d (available from Novagen, Inc.) was digested with restriction enzyme NcoI and BamHI, rendering it linear. pD2 clone containing superoxide dismutase gene was subjected to polymerase chain reaction using two synthetic oligonucleotides and then isolated on agarose gel. The resulting gene segment of 638 bases was treated with restriction enzyme NcoI and BamHI, and linked to the same enzyme-treated pET3d to transform into a host in use for expression, *E. coli* BL21(DE3) (hsdS gal γc I ts857 ind 1 sam7 nin5 lacUV5-T7 genel, Novagen Inc., Madison, Wis., U.S.A.). The used synthetic oligonucleotides were provided by Bio-Synthesis Co. in U.S.A., which were synthesized as we requested. The oligonucleotides included a cleavage site of the used restriction enzyme, and was designed to exactly bind to origin of replication for protein. The sequence of the synthetic oligonucleotides are as follows:

sodF:
5'-GCCTCCACGTTCACCATGGGTGTGCACAAACTGG AACCCAAAG-3' sodR:
5'-GCTAGGCATGTCGGACTTTTACTTGATTGAAGTC CTTGAGGGC-3'

Among the transformed *E. coli* BL21 (DE3) with superoxide dismutase gene, a stronger recombinant clone in degree of expression was selected (KCTC 0288BP) and inoculated on 1 liter of ampicillin(100 ug/ul)-added LB medium. The LB medium was cultured until $OD_{600}$ reached 0.5 at 30° C. IPTG was added so as to be 400 mM, inducing the superoxide dismutase protein to be expressed. After culturing the medium together with shaking for 4 hours, the cell was centrifuged at 4000 g for 10 min and recovered. The resulting cell was dissolved in 25 ml of lysis buffer (20 mM potassium phosphate, pH 7.0, 20 mM NaCl, 0.1 mM EDTA, 0.1 mM PMSF), frozen and thawed three times, and then crushed by operating a sonic generator (Branson sonifier, Model 450) 5 times for 1 min each time. The resulting cell extract was centrifuged at 25,000 g for 1 hour and the supernatant was heat-treated for 1 hour at 80° C. The sample was recentrifuged at 25,000 g for 30 min and the obtained supernatant was isolated on anion exchange chromatography (Q-sepharose, FPLC, LKB Pharmacia) and finally on gel filtration chromatography (Superdex-200, FPLC, LKB Pharmacia). When the purified protein was electrophorated on 16.5% Tricine SDS-polyacrylamide gel, two protein bands of which molecular weight correspond to 24 kDa and 96 kDa were identified (See, FIG. 4). The protein band having the molecular weight of 24 kDa shows almost identical value to 24,344 kDa of SOD molecular weight as calculated from SOD amino acid sequence. The molecular weight of the protein was found to be 24,240 Da exactly by using the mass spectrum. The oligomer having 96 kDa of molecular weight was conformed to the fact that a homotertamer is present in X-ray crystalline construction of *A. pyrophilus* SOD and gel filtration chromatography of Sephacryl S-200 identified that the molecular weight is 89 kDa (See, FIG. 5).

EXAMPLE 3

Metal Analysis of Superoxide Dimutase Protein

In order to find the kind of metals contained in the purified SOD, the results of analysis of the SOD using Atom absorption analyser (Barian SpectrAA800) indicated that 0.75 gram atom of Fe is contained per monomer.

1) For obtaining Fe-free SOD, the obtained SOD protein as above was subjected to dialysis against the following solutions in turn.

(i) 50 mM acetate buffer solution, pH 3.8. 8M urea, 10 mM EDTA, at 25° C. for 16 hours (ii) 50 mM acetate buffer solution, pH 3.8, 8M urea, 1 mM EDTA, at 25° C. for 4 hours (iii) 50 mM potassium phosphate buffer solution, pH 7.0, 8M urea, 1 mM EDTA, at 25° C. for 4 hours (iv) 50 mM potassium phosphate buffer solution, pH 7.0, 1 mM EDTA at 25° C. for 4 hours (v) 50 mM potassium phosphate buffer solution, pH 7.0 at 25° C. for 4 hours.

Thereafter, the protein was finally isolated using desalting column (FPLC, Pharmacia).

2) For obtaining Fe-containing SOD, Fe-free SOD was subjected to dialysis against the following solution at 4° C. in turn.

(i) 50 mM acetate buffer solution, pH 3.8, 8M urea, 10 mM $FeSO_4$ (ii) 50 mM potassium phosphate buffer solution, pH 7.5, 8M urea, 10 mM $FeSO_4$ (iii) 50 mM potassium phosphate buffer solution, pH 7.0, 1 mM $FeSO_4$ (iv) 50 mM potassium phosphate buffer solution, pH 7.0, 0.5 mM EDTA.

Then, centricon was used to concentrate the dialyzed protein to a concentration of 1 mg/ml. Atomic Absorption Spectrophotometer (Barian SectrAA800) was used to measure the reconstituted SOD containing Fe, and then it was found that 0.85 gram atom of Fe is contained per monomer.

Figure 6:
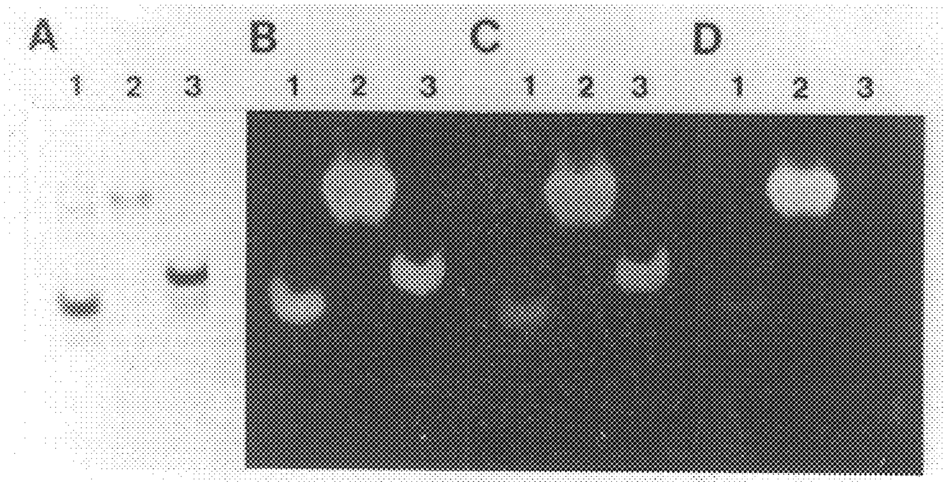
FIG. 6 is a photograph showing the activity of SOD protein as analysed by Nondenaturating gel electrophoresis in the NBT staining method.

It has been reported that several kinds of SODs are inhibited by a certain inhibitor in its activity, respectively, depending on the kind of metal attached thereto. For Cu, Zn-SOD, its activity is inhibited by KCN, and for Fe-SOD, is inhibited by $H_2O_2$. Therefore, in order to examine the ligand metal of the SOD enzyme, *A. pyrophilus* SOD enzyme was previously cultured in 20 mM phosphate buffer solution, pH 7.0 containing two inhibitors, i.e. KCN and $H_2O_2$ and a staining solution was added to the cultured solutions. SOD removed $O_2^-$ to prevent the solution from staining, and thus colorless spots appear in the solutions. *A. pyrophilus* SOD was not inhibited by KCN, but inhibited selectly by $H_2O_2$. As a result, the SOD would be a Fe-SOD (See. FIG. 6).

Figure 7:
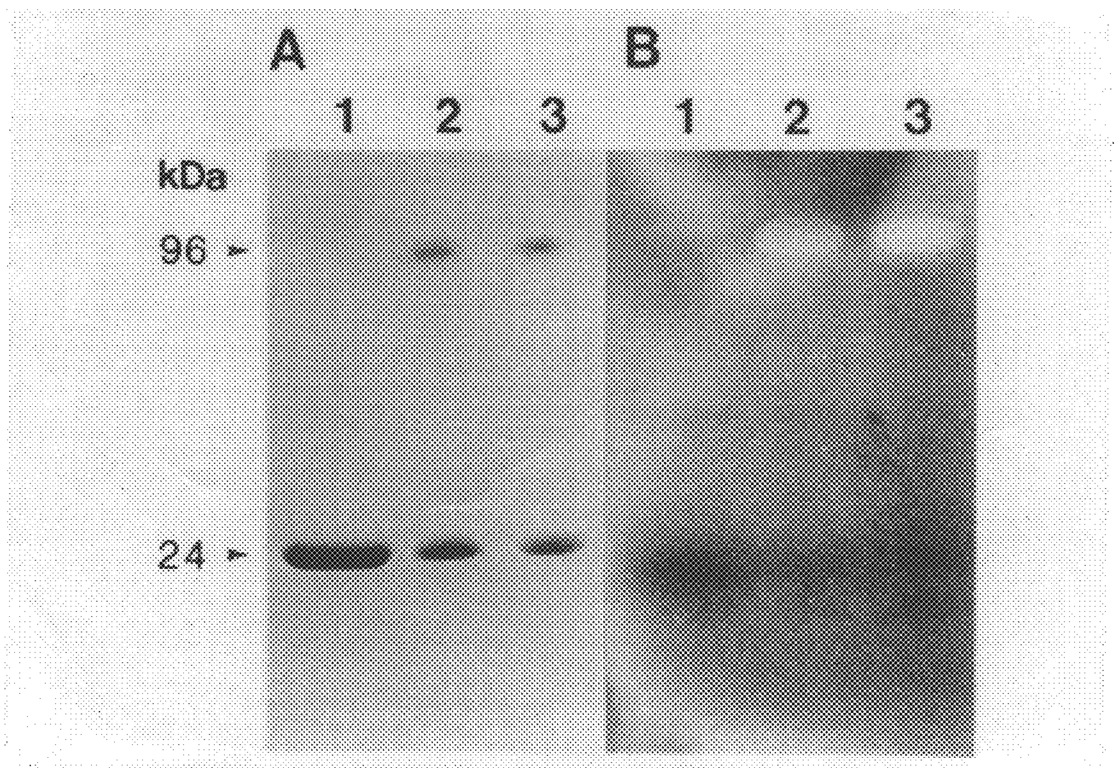
FIG. 7 is a photograph showing Tricine-SDS polyacrylamide gel electrophoresis of a Fe-free SOD and an activated, Fe-bound SOD in the NBT staining method.

Fe-free SOD was made for the purpose of determining enzymic activity of Fe-free SOD and carried out electrophoresis on Tricine SDS-polyacrylamde gel by using NBT staining method (See, FIG. 7). From SDS-PAGE, the Fe-free SOD was found to be present as an inactive monomer and the reconstituted Fe-SOD was found to be present in two forms, i.e., an active tetramer and an inactive monomer. The non-heat treated protein showed the same bands as those of the heat treated protein at 95° C. for 10 min.

EXAMPLE 4

Measurement of Activity of Superoxide Dismutase Protein

When examined in Cytochrome c reduction assay, it was found that specific activity of *A. pyrophilus* SOD was 1,400 units/mg. This value is similar to 1,623 units/mg of Fe-SOD of *E. coli* and 1,387 units/mg of Mn-SOD of *Bacillus stearothennophilus*. Namely, the activity of *A. pyrophilus* at growth optimum temperature could not be compared, but the activity of *A. pyrophilus* at normal temperature was of a similar level to other SOD species.

To observe thermal stability of the enzyme, cytochrome c reduction assay was conducted. The results indicated that *A. pyrophilus* SOD retained approximately 80% of activity even after heating at 95° C. for two hours (See, FIG. 8). To the contrary, *E. coli* Fe-SOD and *Bacillus stearothermophilus* Mn-SOD lost all their activities after heating at 95° C. As a result, it is demonstrated that the isolated enzyme SOD according to the invention has strong thermal activity as expected.

For the purpose of examining stability of the enzyme at various pH, SOD activity was examined at a normal temperature in cytochrome c reduction assay. The results showed the enzyme retained its activity at a range of pH 4.2 to pH 10.7. The kinds of buffer solution used at each pH are as follows: pH 4.0, 4.6: acetate buffer; pH 5.5: citrate buffer; pH 6.2: MES(2-[N-morpholino] ethansulfonic acid) buffer; pH 6.8: BTP (Bis-Tris Propane) buffer; pH 7.0: phosphate buffer; pH 7.5: Hepes buffer; pH 8.2: Tris-Cl buffer; pH 9.2, 10.0, 10.7: carbonate buffer).

Therefore. it was observed that the activity of the enzyme was not lost at all at a range of pH 4.2 to pH 10.0.

What is claimed is:

1. An isolated DNA sequence encoding *Aquifex pyrophilus* superoxide dismutase consisting of SEQ ID NO:2.

2. The isolated DNA sequence of claim 1, wherein said DNA sequence is SEQ ID NO:1.

3. An isolated *A. pyrophilus* superoxide dismutase comprising SEQ ID NO:2 and having a molecular weight of about 96 KDa.

4. The isolated *A. pyrophilus* superoxide dismutase of claim 3 consisting of SEQ ID NO:2.

5. A plasmid comprising the DNA sequence of claim 1.

6. The plasmid of claim 5, wherein said plasmid is pD27.

7. A transformed bacterium comprising the plasmid of claim 5.

8. The transformed bacterium of claim 7, wherein said transformed bacterium is *E. coli* strain BL21(DE3)pD27 (KCTC 0288BP).

9. A synthetic probe which consists of one of the following base sequences:

sodF (SEO ID NO:5):
5'-GCCTCCACGTTCACCATGGGTGTGCACAAAC TGGAACCCAAAG-3' or sodR (SEO ID NO:6):
5'-GCTAGGCATGTCGGACTTTTACTTGATTGAA GTCCTTGAGGGC-3'.

* * * * *

```
                         SEQUENCE LISTING

(1) GENERAL INFORMATION:

   (iii) NUMBER OF SEQUENCES: 6

(2) INFORMATION FOR SEQ ID NO:1:

     (i) SEQUENCE CHARACTERISTICS:
          (A) LENGTH: 2057 base pairs
          (B) TYPE: nucleic acid
          (C) STRANDEDNESS: single
          (D) TOPOLOGY: linear

    (ii) MOLECULE TYPE: DNA (genomic)

    (ix) FEATURE:
          (A) NAME/KEY: CDS
          (B) LOCATION: 1014..1652

    (xi) SEQUENCE DESCRIPTION: SEQ ID NO:1:

GAGCTCCTGG GCGAACTCGT CGTTGAGTTC GGGGAGAACC TTCTTCTTTA TCTCCTTTAT     60

CTTAACCTTT ATATTTACCT TCCTTATCTC CTTGCCTTCC TGGTCGTACA GGGGAAGCTC    120

TTTCAGCTCT ACCTCCTTCT CCCGCCTTCT TTCCTTTAAG GGCTTCCTCT ACTTCCTTTC    180

TCAGCATTCC CTGGCCGAGT ATCACCGAGG TTTCCTGCTT TACCTTTTCC CCTTCACCGC    240

CAACCTCTTC AACTTCGTAC TCAAGGACGA GCATATCCCC CTCTTGGGCC GGCTCGTTCT    300

CTTCCTTTGG GTTCCCAAAC CGCGTTAGCC TCTCTTAGTC TTTCAAGCTC TTCCTTACAT    360

ACTCCTCCTT GAACTCTATC TTGGGAACTT CTACCTCAAG GTCTGCGATG TTTTTTAGCT    420
```

-continued

```
CAAACTCTGG AGCGACTTCA AAGCTAACGG TGTATTTTAC GCTTCCCTCT TCCTCATTTA    480

CCTCAAGTTT TTCAAGGAAT ACGTCCGCAA CGGGTCTTAT ATTTGCCTTC TCAAGGGCTT    540

CCTGGAGTGT TTCGTCCGCT ATTTTCTTTC CAACCTCTTC CTCCACGTAG TCCTTATACT    600

TCGCTCTAAT TATCCAGAGT GGGGCTTTTC CCCTTCTGAA TCCCTGTATC TGGACGTTCT    660

GCTGCAGGTT CTTGTAGGTT TCCTCAAGTT TTTCCTTAAC CTTTTGGTCC TTTACCTCAA    720

CCGTTAGGGA TTTAAAGAGT CCTTCCCTGT CCTGAACCTC TACTTTCATT ACGACCTCCG    780

TCTATTTTAC TGGTGCGGGT GGCGGGAGTC GAACCCGCAC GCCCTTACGG GCACCGGATC    840

CTAAGTCCGG CGCGTCTGCC AGTTCCGCCA ACACCCGCTA AATAAATTAT TATATAGTTC    900

GCAAACGTGA AAAAAAGAAT CCTTTCTTTT ATGACCTTAG GCATATAAAA CCTTAAAACT    960

TCCAAGTTAA AATTTTTAAA TAGAAAAAAG CTAACGAAAA GGAGGTGGCA AAA ATG      1016
                                                           Met
                                                             1

GGT GTG CAC AAA CTG GAA CCC AAA GAC CAT TTA AAA CCT CAA AAC CTT     1064
Gly Val His Lys Leu Glu Pro Lys Asp His Leu Lys Pro Gln Asn Leu
              5                  10                  15

GAG GGT ATA TCT AAC GAA CAG ATA GAA CCC CAC TTT GAG GCA CAC TAC     1112
Glu Gly Ile Ser Asn Glu Gln Ile Glu Pro His Phe Glu Ala His Tyr
         20                  25                  30

AAG GGT TAC GTT GCA AAG TAT AAC GAG ATT CAG GAG AAA CTC GCG GAC     1160
Lys Gly Tyr Val Ala Lys Tyr Asn Glu Ile Gln Glu Lys Leu Ala Asp
     35                  40                  45

CAG AAC TTT GCG GAC AGA AGC AAG GCA AAC CAG AAC TAC TCC GAA TAC     1208
Gln Asn Phe Ala Asp Arg Ser Lys Ala Asn Gln Asn Tyr Ser Glu Tyr
 50                  55                  60                  65

AGG GAG TTG AAG GTT GAA GAA ACT TTT AAC TAC ATG GGG GTG GTG CTC     1256
Arg Glu Leu Lys Val Glu Glu Thr Phe Asn Tyr Met Gly Val Val Leu
                 70                  75                  80

CAC GAG CTT TAC TTC GGC ATG CTC ACG CCT GGT GGA AAG GGA GAA CCC     1304
His Glu Leu Tyr Phe Gly Met Leu Thr Pro Gly Gly Lys Gly Glu Pro
             85                  90                  95

TCC GAA GCC CTC AAG AAG AAG ATT GAA GAG GAT ATC GGA GGA CTT GAT     1352
Ser Glu Ala Leu Lys Lys Lys Ile Glu Glu Asp Ile Gly Gly Leu Asp
        100                 105                 110

GCC TGC ACG AAC GAG CTA AAG GCC GCA GCT ATG GCC TTC AGG GGA TGG     1400
Ala Cys Thr Asn Glu Leu Lys Ala Ala Ala Met Ala Phe Arg Gly Trp
    115                 120                 125

GCT ATA CTC GGG CTT GAC ATA TTC AGC GGA AGG CTC GTG GTT AAC GGA     1448
Ala Ile Leu Gly Leu Asp Ile Phe Ser Gly Arg Leu Val Val Asn Gly
130                 135                 140                 145

CTT GAC GCC CAC AAC GTT TAT AAC TTA ACG GGA CTC ATT CCC CTC ATA     1496
Leu Asp Ala His Asn Val Tyr Asn Leu Thr Gly Leu Ile Pro Leu Ile
                150                 155                 160

GTT ATA GAC ACT TAT GAA CAC GCC TAC TAC GTT GAC TAC AAG AAC AAG     1544
Val Ile Asp Thr Tyr Glu His Ala Tyr Tyr Val Asp Tyr Lys Asn Lys
            165                 170                 175

AGA CCT CCT TAC ATT GAC GCA TTC TTC AAG AAC ATA AAC TGG GAC GTC     1592
Arg Pro Pro Tyr Ile Asp Ala Phe Phe Lys Asn Ile Asn Trp Asp Val
        180                 185                 190

GTT AAC GAA AGG TTT GAA AAG GCT ATG AAA GCT TAC GAG GCC CTC AAG     1640
Val Asn Glu Arg Phe Glu Lys Ala Met Lys Ala Tyr Glu Ala Leu Lys
    195                 200                 205

GAC TTC ATC AAG TAAGCTTGCT CCCTTTTCTC CTTTCCCTTC TCCTTATCCT         1692
Asp Phe Ile Lys
210
```

-continued

```
ATCCTGCGGG TATAAAAAGC TCTCCAAAAC CACTCCCGGA ACCAATTTTT ACACTTAAAA   1752

GAATCGGAGA TTACGTTTAC GTAATAGGCG AGGACATTGA GGTAAAGGGC TTTAAAAAGC   1812

ATAAAAACTT CTGGTATAAG AAGGAAGAAA GGGCCTTCTG TTTTTACGTT AAGCATGTTA   1872

AAGGTAAAGA GAAAAAAGCC TGCGTTCCCG AGGCGGGTCG GATAAAGCCG AGAATTTCAT   1932

ACGAAGAGAA AGAAGAGAAG GTCATTATAA GGGCTGAGGA AAAGGGAATT TACAACGTTT   1992

ATCCTTATGA GGGAAACCTA TTGATACCTT TTCCCTTAAA AACCTTTGAA GACTCTGCAG   2052

AGCTC                                                               2057
```

(2) INFORMATION FOR SEQ ID NO:2:

(i) SEQUENCE CHARACTERISTICS:
(A) LENGTH: 213 amino acids
(B) TYPE: amino acid
(D) TOPOLOGY: linear (ii) MOLECULE TYPE: protein (xi) SEQUENCE DESCRIPTION: SEQ ID NO:2:

```
Met Gly Val His Lys Leu Glu Pro Lys Asp His Leu Lys Pro Gln Asn
  1               5                  10                  15

Leu Glu Gly Ile Ser Asn Glu Gln Ile Glu Pro His Phe Glu Ala His
             20                  25                  30

Tyr Lys Gly Tyr Val Ala Lys Tyr Asn Glu Ile Gln Glu Lys Leu Ala
         35                  40                  45

Asp Gln Asn Phe Ala Asp Arg Ser Lys Ala Asn Gln Asn Tyr Ser Glu
     50                  55                  60

Tyr Arg Glu Leu Lys Val Glu Glu Thr Phe Asn Tyr Met Gly Val Val
 65                  70                  75                  80

Leu His Glu Leu Tyr Phe Gly Met Leu Thr Pro Gly Gly Lys Gly Glu
                 85                  90                  95

Pro Ser Glu Ala Leu Lys Lys Lys Ile Glu Glu Asp Ile Gly Gly Leu
            100                 105                 110

Asp Ala Cys Thr Asn Glu Leu Lys Ala Ala Ala Met Ala Phe Arg Gly
        115                 120                 125

Trp Ala Ile Leu Gly Leu Asp Ile Phe Ser Gly Arg Leu Val Val Asn
    130                 135                 140

Gly Leu Asp Ala His Asn Val Tyr Asn Leu Thr Gly Leu Ile Pro Leu
145                 150                 155                 160

Ile Val Ile Asp Thr Tyr Glu His Ala Tyr Tyr Val Asp Tyr Lys Asn
                165                 170                 175

Lys Arg Pro Pro Tyr Ile Asp Ala Phe Phe Lys Asn Ile Asn Trp Asp
            180                 185                 190

Val Val Asn Glu Arg Phe Glu Lys Ala Met Lys Ala Tyr Glu Ala Leu
        195                 200                 205

Lys Asp Phe Ile Lys
    210
```

(2) INFORMATION FOR SEQ ID NO:3:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: DNA (genomic)

-continued (xi) SEQUENCE DESCRIPTION: SEQ ID NO:3:

GAAAAGGAGG 10

(2) INFORMATION FOR SEQ ID NO:4:

(i) SEQUENCE CHARACTERISTICS:
(A) LENGTH: 6 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:4:

TATAAA 6

(2) INFORMATION FOR SEQ ID NO:5:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC PRIMER"

(xi) SEQUENCE DESCRIPTION: SEQ ID NO:5:

GCCTCACGTT CACCATGGGT GTGCACAAAC TGGAACCCAA AG 42

(2) INFORMATION FOR SEQ ID NO:6:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "SYNTHETIC PRIMER"

(xi) SEQUENCE DESCRIPTION: SEQ ID NO:6:

GCTAGGCATG TCGGACTTTT ACTTGATGAA GTCCTTGAGG GC 42